United States Patent [19]
Adelman et al.

[11] Patent Number: 6,111,135
[45] Date of Patent: Aug. 29, 2000

[54] MANUFACTURE OF 1,3-PROPANEDIOL ESTERS FROM FORMALDEHYDE AND ETHYLENE USING A MODIFIED PRINS REACTION

[75] Inventors: Douglas J. Adelman, Wilmington; Neville Everton Drysdale, Newark, both of Del.

[73] Assignee: E. I. du Pont de Nemours and Company, Wilmington, Del.

[21] Appl. No.: 09/203,985

[22] Filed: Dec. 2, 1998

Related U.S. Application Data

[60] Provisional application No. 60/082,552, Apr. 21, 1998, and provisional application No. 60/067,934, Dec. 8, 1997.

[51] Int. Cl.[7] .................................................... C07C 67/00
[52] U.S. Cl. .............................................................. 560/238
[58] Field of Search .............................................. 560/238

[56] References Cited

U.S. PATENT DOCUMENTS 4,322,355  3/1982  Horvitz et al. ........................ 260/340.7

FOREIGN PATENT DOCUMENTS 51-143605  12/1976  Japan .............................. C07C 67/00
51-143606  12/1976  Japan .............................. C07C 31/18

OTHER PUBLICATIONS

B.B. Snyder in B. Trost et al., Ed., Comprehensive Organic Synthesis, 2, Pergamon Press, Oxford, 527–534, 1991.

D.R. Adams, et al., *Synthesis*, 661–672, 1977.

*Primary Examiner*—Gary Geist
*Assistant Examiner*—Robert W. Deemie

[57] ABSTRACT

Disclosed is a process for manufacturing an ester of 1,3-propanediol, comprising, contacting at a temperature of about 0° C. to about 250° C., ethylene, formaldehyde or a form of formaldehyde, a carboxylic acid, and a compound of the formula $MZ_n.Q_t$, wherein:

M is a zirconium[IV], cobalt[II], vanadium[IV], bismuth [II], tin[II], a rare earth metal, scandium or yttrium;

n is the oxidation state of M;

at least one of Z is an anion of the formula $R^1SO_3^-$ or $R^1CO_2^-$, wherein $R^1$ is hydrocarbyl or substituted hydrocarbyl containing 1 to 20 carbon atoms or part of a polymer, and the remainder of Z is oxo or one or more monovalent anions;

Q is a neutral ligand; and t is 0 or an integer of 1 to 12.

23 Claims, No Drawings

MANUFACTURE OF 1,3-PROPANEDIOL ESTERS FROM FORMALDEHYDE AND ETHYLENE USING A MODIFIED PRINS REACTION

This application claims priority benefit of U.S. Provisional Application Serial No. 60/082,552, filed Apr. 21, 1998 and priority benefit of U.S. Provisional Application Serial No. 60/067,934, filed Dec. 8, 1997.

FIELD OF THE INVENTION

The invention generally relates to the selective preparation of 1,3-propanediol esters, preferably diesters, by contacting ethylene, formaldehyde, or a form of formaldehyde, and a carboxylic acid in the presence of a perfluoroalkylsulfonate or perfluorocarboxylate. Moreover, formic acid can be used as the carboxylic acid in improved Prins reactions to make esters.

BACKGROUND OF THE INVENTION 1,3-Propanediol or its reactive derivatives are useful in many applications, for example as chemical intermediates and as monomers for polyesters and other types of condensation polymers. However, the uses of these compounds have been retarded by the relative difficulty, and hence high cost, of making them. Thus, improved, lower cost methods of making such compounds are desired.

The "Prins" reaction has been known for a long time to make 1,3-diols. In this reaction an olefin is often reacted with formaldehyde (or another aldehyde) to form a 1,3-diol (or its mono- or diester if a carboxylic acid is present) or a cyclic ether of some sort, in the presence of a strong Bronsted or Lewis acid, although oftentimes there are large amounts of byproducts, see for instance B. B. Snyder in B. Trost, et al., Ed., Comprehensive Organic Synthesis, Vol. 2, Pergamon Press, Oxford, 1991, p. 527–534, and D. R. Adams, et al., Synthesis, 1977, p. 661–672. Selectivity in the Prins reaction is sometimes difficult, due to the large variety of possible products. In order to make 1,3-propanediol or its derivatives it would be necessary to use ethylene as the olefin, and it is well known that ethylene does not react well in the Prins reaction, see for instance, Japanese Patent Applications 51-143,606 and 51-143,605 which describe the preparation of 1,3-propanediols and its esters from ethylene, formaldehyde and carboxylic acid, using a Bronsted acid catalyst.

What are needed are processes for manufacturing diesters of 1,3-propanediol which do not have the deficiencies of the prior art. Other objects and advantages of the present invention will become apparent to those skilled in the art upon reference to the detailed description which hereinafter follows.

SUMMARY OF THE INVENTION

The invention relates to a first process for manufacturing an ester of 1,3-propanediol, comprising, contacting at a temperature of about 0° C. to about 250° C., ethylene, formaldehyde or a form of formaldehyde, a carboxylic acid, and a compound of the formula $MZ_n \cdot Q_t$, wherein:

M is a zirconium[IV], cobalt[II], vanadium[IV], bismuth [II], tin[II], hydrogen, a rare earth metal, scandium or yttrium;

n is the oxidation state of M;

at least one of Z is an anion of the formula $R^1SO_3^-$ or $R^1CO_2^-$, wherein $R^1$ is hydrocarbyl or substituted hydrocarbyl containing 1 to 20 carbon atoms or part of a polymer, and the remainder of Z is oxo or one or more monovalent anions;

Q is a neutral ligand; and t is 0 or an integer of 1 to 12.

This invention also concerns a second process for the production of an ester by the Prins reaction by reacting an olefin, formaldehyde or a form of formaldehyde, and a carboxylic acid and optionally in the presence of a Lewis or Bronsted acid catalyst, wherein the improvement comprises, using formic acid as the carboxylic acid.

DETAILED DESCRIPTION OF THE PREFERRED EMBODIMENTS

By a "rare earth metal" is meant one of lanthanum, cerium, praeseodymium, neodymium, promethium, samarium, europium, gadolinium, terbium, dysprosium, holmium, erbium, thulium, ytterbium, or lutetium. The rare earth metal may also be a mixture of rare earth metals, especially "mischmetall", a mixture of rare earth metals having the approximate relative abundance's of the natural ore from which the metals are recovered. Numbers within brackets indicate the oxidation state of the M. It is preferred that M is a metal (not hydrogen), and more preferably that M is a rare earth metal, scandium or yttrium and n is 3.

By hydrocarbyl is meant a univalent radical containing only carbon and hydrogen. By substituted hydrocarbyl is meant hydrocarbyl substituted with one or more functional groups which do not interfere with the use the salt containing that radical in the processes herein.

At least one of Z must be $R^1CO_2^-$ or $R^1SO_3^-$, preferably $R^1SO_3^-$. Preferably, $R^1$ is perfluoroalkyl containing 1 to 12 carbon atoms, and optionally containing one or more ether groups, or part of a fluorinated polymer wherein the carbon atoms alpha and beta to the sulfonate or carboxylate group are together bonded to at least 4 fluorine atoms. In another preferred form, when $R^1SO_3^-$ is present R1 is aryl or substituted aryl (substituted here having the same meaning as in "substituted hydrocarbyl"). $R^1SO_3^-$ may be part of a polymer (as in $-CF_2CF_2SO_3^-$), such as a salt of the perfluorinated polymer sold under the name Nafion® by E. I. du Pont de Nemours and Company, Wilmington, Del., U.S.A., or an ethylene copolymer of a partially fluorinated olefin containing a sulfonic acid group as described in World Patent Application WO 96/23010. Similarly, $R^1CO_2^-$ may also be part of a polymer. More preferably, $R^1$ is trifluoromethyl, this anion herein sometimes being referred to as triflate as $R^1SO_3^-$, and trifluoroacetate as $R^1CO_2^-$.

Preferably, all three of "Z" in the rare earth metal compound are $R^1SO_3^-$ or $R^1CO_2^-$. Other groups which may also be present in the metal compound are well known in the art, see for instance, U.S. Pat. No. 5,541,346, which is hereby included by reference. If an oxo anion is present it "occupies" two positive charges on the metal ion, since the oxo anion is divalent. In this instance the remaining anion will be $R^1SO_3^-$. The metal catalysts may also be in a heterogeneous form, for instance on a support such as alumina. Such forms and their preparation are also described in U.S. Pat. No. 5,541,346.

Q may be any neutral (uncharged) ligand, such as an ether, amine, water, alcohol, etc. It is preferred that t is 0. In the overall composition of $MZ_n \cdot Q_t$, t may actually be a fractional number, but this is usually indicative of a mixture of compounds in which t varies.

The carboxylic acid may be any carboxylic acid, and may be substituted with any functional group (other than carboxyl) which does not interfere with the reaction. The carboxylic acid may have one or more carboxyl groups per molecule, but it is preferred that the carboxylic acid be monofunctional or difunctional, more preferably monofunctional. Useful carboxylic acids include formic, acetic, benzoic, adipic, succinic, terephthalic, and o-, m- and p-toluic acids. Preferred carboxylic acids are acetic and formic acids, and formic acid is more preferred. If a difunctional carboxylic acid is used, the product may include oligomers and/or polymers of the difunctional carboxylic acid and 1,3-propanediol. It is preferred that the carboxylic acid itself have a ("first", if it contains more than one carboxyl group) pKa of about 2 to about 6 when measured in water.

Formic acid is especially preferred in the first process, because, in this reaction, to form a diester when formic acid is used to make 1,3-propanediol diformate it is much more selective for the desired product then when other carboxylic acids, such as acetic acid, are used. In the second process herein ethylene, is a preferred olefin.

Formaldehyde itself, or any of the forms of formaldehyde, may be used. By a "form of formaldehyde" is meant a compound that readily decomposes under process conditions to give formaldehyde, such as trioxane, paraformaldehyde, and formaldehyde acetals or hemiacetals.

Ethylene is another reactant in the first or second process. While its concentration is not critical, it is preferred that the ethylene pressure be about atmospheric pressure (0 Pag, gauge) to about 70 MPa, preferably about 700 kPag to about 10 MPa, more preferably about 700 kPag to about 1.4 MPa. Other olefins may be used in the second process.

The molar ratio (starting ratio if a batch or semibatch reaction) of carboxylic acid:formaldehyde in the process is not critical, but in order to fully utilize the reactants (assuming all the formaldehyde is reacted) a molar ratio of at least 2:1 is preferred, and a range of about 2:1 to about 15:1 is more preferred, and a range of about 3:1 to about 8:1 is especially preferred. If it is desired to make an oligomer or polymer of a difunctional carboxylic acid, a molar ratio of about 2:1 is desirable.

The temperature at which the first process is carried out is about 0° C. to about 250° C., preferably about 50° C. to about 175° C. The reaction is preferably carried out in a liquid medium. The medium preferably dissolves at least some of the formaldehyde and ethylene. Preferably, the liquid medium is one or more of the carboxylic acid and/or products, although inert liquids such as aromatic hydrocarbons may be used also. Water may be present during the reaction which is convenient because some of the ingredients such as formic acid and formaldehyde are available as aqueous solutions. The products of the reaction may be separated by fractional distillation if they are not oligomers or polymers. The process may be run in a variety of ways, for instance by batch, semibatch or continuous methods.

The metal salt catalyst may be recovered and reused, see for instance U.S. Pat. No. 5,541,346. Assuming the salt is soluble and stable in water, the reaction mixture may be extracted with water, and the water (and any other water soluble species) evaporated to recover the catalyst, which may then be dried by heating. If the metal salt is insoluble in the process medium, it may simply be filtered off, optionally dried, and reused.

In the second process the "normal" conditions for Prins reactions are used. In addition to the formic acid which is present, the reaction may optionally be carried out in the presence of a Lewis acid or a Bronsted acid which may act as a catalyst, the latter in addition to the formic acid already present. In one preferred embodiment a Lewis or Bronsted acid is present. In another preferred embodiment the Lewis and Bronsted acids are not present. A preferred olefin for the second process is ethylene.

The product(s) of the first and second processes in which ethylene and formaldehyde are used are mono- or diesters of a diol, preferably 1,3-propanediol. It is preferred that at least one of the products is the diester. Typical byproducts in these reactions are

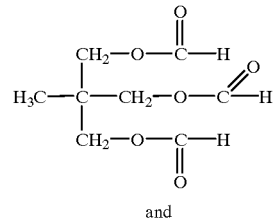

(I)

and

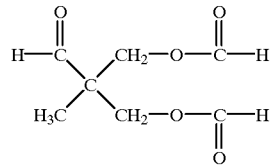

(II)

These byproducts, and others, may be minimized to some extent by the process conditions used. For instance use of the metal catalyst of the first process, and/or using relatively high molar ratios of formic acid to formaldehyde in the process will tend to minimize these byproducts.

EXAMPLES 1–49

In a dry box, to an oven dried shaker tube were added the following: triflate (OTf is triflate) or trifluoroacetate (TFA is trifluoroacetate) catalyst, carboxylic acid, and formaldehyde, either paraformaldehyde, 55% aqueous formaldehyde, or trioxane. Glacial acetic acid or 96% formic acid (remainder water) was used. The tube, which had a hole in it throughout the process to admit ethylene, was closed and then placed in a shaker apparatus where it was heated to the desired temperature, and pressurized with ethylene to 6.9 MPa. After about 16 h, the apparatus was cooled to room temperature, the gases vented and the resulting reaction mixture was analyzed via Gas Chromatography (GC) using a flame ionization detector.

Specific reaction conditions and results are given in Table 1. The 1,3-dioxane (GC area %) represents the percentage of the area on the GC trace attributable to 1,3-dioxane, and is a rough measure of the weight percent of 1,3-dioxane. Similarly, the area percentage of the 1,3-propanediol diester produced is also given. These area percents are percentages of the total reaction mixtures, including any starting materials present. Blank tests indicated that formic acid decomposed in the GC and was not detected, but acetic acid was stable and part of the area percents calculated. Other unlisted products were also present in the product mixtures, although visual inspection of the GC traces indicated that reactions with formic acid had fewer byproducts than similar reactions with acetic acid. With formic acid, one of the byproducts was believed to be 1,1,1,-tris(hydroxymethyl)ethane triformate.

TABLE 1

| Ex. No. | Acid | Acid g | Formaldehyde[a] | Rxn. Temp., °C | Catalyst[b] (g) | 1,3-Dioxane (GC Area %) | 1,3-PDO Diester (GC Area %) |
|---|---|---|---|---|---|---|---|
| 1 | Formic | 0.575 | 0.375 | 130 | Yb(OTf)$_3$ (0.125) | 3.85 | 31.77 |
| 2 | Formic | 1.15 | 0.375 | 130 | Yb(OTf)$_3$ (0.125) | 0.77 | 49.76 |
| 3 | Formic | 1.725 | 0.375 | 130 | Yb(OTf)$_3$ (0.125) | 0 | 58.12 |
| 4 | Formic | 2.3 | 0.375 | 130 | Yb(OTf)$_3$ (0.125) | 0 | 66.17 |
| 5 | Formic | 1.15 | 0.75 | 130 | Yb(OTf)$_3$ (0.125) | 2.26 | 38.1 |
| 6 | Formic | 1.15 | 1.125 | 130 | Yb(OTf)$_3$ (0.125) | 10.49 | 18.07 |
| 7 | Formic | 1.15 | 1.5 | 130 | Yb(OTf)$_3$ (0.125) | 10.83 | 17.59 |
| 8 | Formic | 1.15 | 2.25 | 130 | Yb(OTf)$_3$ (0.125) | 14.67 | 8.87 |
| 9 | Formic | 1.15 | 3 | 130 | Yb(OTf)$_3$ (0.125) | 21.47 | 6.46 |
| 10 | Formic | 2.3 | 0.375 | 130 | Yb(OTf)$_3$ (0.025) | 0 | 54.18 |
| 11 | Formic | 2.3 | 0.375 | 130 | Yb(OTf)$_3$ (0.05) | 0 | 51.18 |
| 12 | Formic | 2.3 | 0.375 | 130 | Yb(OTf)$_3$ (0.075) | 0 | 46.73 |
| 13 | Formic | 2.3 | 0.375 | 130 | Yb(OTf)$_3$ (0.100) | 0 | 62.14 |
| 14 | Formic | 2.3 | 0.375 | 130 | Yb(OTf)$_3$ (0.125) | 0 | 62.49 |
| 15 | Formic | 1.725 | 0.375 | 130 | Yb(OTf)$_3$ (0.025) | 2.28 | 44.24 |
| 16 | Formic | 1.725 | 0.375 | 130 | Yb(OTf)$_3$ (0.05) | 0 | 55.61 |
| 17 | Formic | 1.725 | 0.375 | 130 | Yb(OTf)$_3$ (0.075) | 0 | 47.57 |
| 18 | Formic | 1.725 | 0.375 | 130 | Yb(OTf)$_3$ (0.100) | 0 | 49.93 |
| 19 | Formic | 1.725 | 0.375 | 130 | Yb(OTf)$_3$ (0.125) | 0 | 57.06 |
| 20 | Formic | 1.725 | 0.375 | 100 | Yb(OTf)$_3$ (0.025) | 8.87 | 43.19 |
| 21 | Formic | 1.725 | 0.375 | 100 | Yb(OTf)$_3$ (0.05) | 8.24 | 42.73 |
| 22 | Formic | 1.725 | 0.375 | 100 | Yb(OTf)$_3$ (0.075) | 8.59 | 40.5 |
| 23 | Formic | 1.725 | 0.375 | 100 | Yb(OTf)$_3$ (0.100) | 6.52 | 39.83 |
| 24 | Formic | 1.725 | 0.375 | 100 | Yb(OTf)$_3$ (0.125) | 4.42 | 48.72 |
| 25 | Formic | 2.3 | 0.375 | 70 | Yb(OTf)$_3$ (0.025) | 5.12 | 20.52 |
| 26 | Formic | 2.3 | 0.375 | 70 | Yb(OTf)$_3$ (0.05) | 5.99 | 22.72 |
| 27 | Formic | 2.3 | 0.375 | 70 | Yb(OTf)$_3$ (0.075) | 7.66 | 28.33 |
| 28 | Formic | 2.3 | 0.375 | 70 | Yb(OTf)$_3$ (0.100) | 7.56 | 32.31 |
| 29 | Formic | 2.3 | 0.375 | 70 | Yb(OTf)$_3$ (0.125) | 5.05 | 20.28 |
| 30 | Acetic | 1.5 | T 0.50 | 130 | Yb(OTf)$_3$ (0.125) | 2.11 | 12.4 |
| 31 | Acetic | 1.5 | T 0.40 | 130 | Yb(OTf)$_3$ (0.125) | 1.31 | 12.1 |
| 32 | Acetic | 1.5 | T 0.30 | 130 | Yb(OTf)$_3$ (0.125) | 1.56 | 14.61 |
| 33 | Acetic | 1.5 | T 0.20 | 130 | Yb(OTf)$_3$ (0.125) | 0.52 | 10.64 |
| 34 | Acetic | 1.5 | T 0.10 | 130 | Yb(OTf)$_3$ (0.125) | 0.18 | 5.56 |
| 35 | Acetic | 4.5 | 0.75 | 100 | Yb(OTf)$_3$ (0.25) | 0.6 | 1.88 |
| 36 | Acetic | 4.5 | 0.75 | 100 | Y(OTf)$_3$ (0.25) | 0.66 | 0.83 |
| 37 | Acetic | 4.5 | 0.75 | 100 | La(OTf)$_3$ (0.25) | 0 | 0 |
| 38 | Acetic | 4.5 | 0.75 | 100 | Sc(OTf)$_3$ (0.25) | 1.75 | 7.45 |
| 39 | Acetic | 4.5 | 0.75 | 100 | Er(OTf)$_3$ (0.25) | 0 | 0 |
| 40 | Formic | 2.3 | 0.375 | 130 | Co(OTf)$_2$ (0.125) | 0.78 | 47.67 |
| 41 | Formic | 2.3 | 0.375 | 130 | Dy(TFA)$_3$ (0.125) | 8.82 | 28.16 |
| 42 | Formic | 2.3 | 0.375 | 130 | Cp*$_2$Zr(OTf)$_2$ (0.125) | 0 | 58.46 |
| 43 | Formic | 2.3 | 0.375 | 130 | Cp$_2$V(OTf)$_2$ (0.125) | 0 | 54.74 |
| 44 | Formic | 2.3 | 0.375 | 130 | p-toluenesulfonic acid (0.125) | 0 | 54.74 |
| 45 | Formic | 2.3 | 0.375 | 130 | Nafion ® NR-50 (0.125) | 0 | 42.6 |
| 46 | Formic | 2.3 | Aq 0.68 | 130 | Yb(OTf)$_3$ (0.125) | 4.65 | 36.8 |
| 47 | Formic | 2.3 | 0.375 | 130 | La(TFA)$_3$ (0.125) | 0 | 49.65 |
| 48 | Formic | 2.3 | 0.375 | 130 | Sn(OTf)$_2$ (0.125) | 0 | 52.62 |
| 49 | Formic | 2.3 | 0.375 | 130 | Bi(OTf)$_3$ (0.125) | 0 | 62.7 |

[a]All paraformaldehyde except those marked "T", which were trioxane, or 55% aqueous formaldehyde, marked "Aq".
[b]Cp is cyclopentadienyl and Cp* is pentamethylcyclopentadienyl.

EXAMPLE 50

To a 1 liter stainless steel autoclave were added 470 ml of aqueous 96 wt % formic acid (Aldrich Chemical Co., Milwaukee. Wis., U.S.A.) and 30 g of paraformaldehyde (Aldrich). The autoclave was sealed and stirred for 10 min while being purged with nitrogen. It was then pressurized to 5.2 MPa ethylene and heated to 130° C. When it reached 130° C., the ethylene pressure was adjusted to 6.9 MPa. The autoclave was stirred and held at 130° C. for 4 h. After cooling, the ethylene was vented and the liquid phase recovered. GC analysis, using an internal standard method, indicated that 10 percent of the paraformaldehyde was converted to 1,3-propanediol diformate.

EXAMPLES 51–53

Each of these Examples was run twice. The first column giving % 1.3-propanediol diformate is after heating for 14 h, while the second column is after heating for 16 h. The reason for the difference in yields is not known.

EXAMPLE 51

In a dry box, formic acid (96%) (2.3, 3.08, 4.60, 6.13 and 7.66 g) was added to each of five separate oven dried 25 mL vials. Paraformaldehyde (0.10 g) and ytterbium triflate (0.03 g) were added to each vial. The vials were pressurized to about 6.9 MPa with ethylene, sealed and then heated to 130° C. After approximately 14 h the reactions were cooled to room temperature and the gases vented. GC analysis of the reaction crudes gave the yields reported in Table 2, based on formaldehyde, via an internal standard method.

TABLE 2

| Run | Formic acid (g) | 1,3-Propanediol diformate (%) | |
|---|---|---|---|
| A | 2.30 | 23.49 | 21.67 |
| B | 3.08 | 24.92 | 27.56 |
| C | 4.60 | 23.83 | 21.20 |
| D | 6.13 | 30.10 | 23.17 |
| E | 6.66 | 33.97 | 22.52 |

EXAMPLE 52

In a dry box, formic acid (96%) (2.3, 3.08, 4.60, 6.13 and 7.66 g) was added to each of five separate oven dried 25 mL vials. Aqueous 55% formaldehyde (0.180 g) and ytterbium triflate (0.03 g) were added to each vial. The vials were pressurized to about 6.9 MPa with ethylene, sealed and then heated to 130° C. After approximately 14 h the reactions were cooled to room temperature (RT) and the gases vented. GC analysis of the reaction crudes gave the yields reported in Table 3, based on formaldehyde, via an internal standard method.

TABLE 3

| Entry | Formic acid (g) | 1,3-Propanediol diformate (%) | |
|---|---|---|---|
| A | 2.30 | 18.36 | 12.89 |
| B | 3.08 | 33.59 | 17.27 |
| C | 4.60 | 48.80 | 20.83 |
| D | 6.13 | 39.87 | 19.68 |
| E | 6.66 | 39.10 | 19.19 |

EXAMPLE 53

In a dry box, formic acid (96%) (2.3, 3.08, 4.60, 6.13 and 7.66 g) was added to each of five separate oven dried 25 mL vials. Aqueous 37% formaldehyde (0.270 g) and ytterbium triflate (0.03 g) were added to each vial. The vials were pressurized to about 6.9 MPa with ethylene, sealed and then heated to 130° C. After approximately 14 h the reactions were cooled to room temperature and the gases vented. GC analysis of the reaction crudes gave the yields shown in Table 4, based on formaldehyde, via an internal standard method.

TABLE 4

| Entry | Formic acid (g) | 1,3-Propanediol diformate (%) | |
|---|---|---|---|
| A | 2.30 | 26.69 | 14.77 |
| B | 3.08 | 49.03 | 17.28 |
| C | 4.60 | 54.38 | 18.71 |
| D | 6.13 | 57.36 | 14.05 |
| E | 6.66 | 56.83 | 20.47 |

EXAMPLE 54

Reaction of Ethylene, Paraformaldehyde, Formic acid and Scandium Triflate

In a dry box, formic acid (96%) (3.08 g) and paraformaldehyde (0.10 g) were added to each of five separate oven dried 25 mL vials. Scandium triflate (0.10, 0.2, 0.3, 0.4 and 0.5 g) was then added. The vials were pressurized with ethylene so that the final pressure would be 6.9 MPa at temperature (90° C.). After approximately 14 h, the reactions were cooled to room temperature and the gases vented. $^1$H NMR analyses of the samples gave the following yields of 1,3-propanediol diformate based on formaldehyde, as shown in Table 5.

TABLE 5

| Entry | Scandium Triflate (g) | 1,3-Propanediol diformate (%) |
|---|---|---|
| 1 | 0.1 | 37.61 |
| 2 | 0.2 | 27.78 |
| 3 | 0.3 | 33.13 |
| 4 | 0.4 | 38.99 |
| 5 | 0.5 | 41.45 |

EXAMPLE 55

Reaction of Ethylene Paraformaldehyde, Formic acid and Scandium Triflate

In a dry box, formic acid (96%) (3.08 g) and paraformaldehyde (0.10 g) were added to each of five separate oven dried 25 mL vials. Scandium triflate (0.10, 0.2, 0.3, 0.4 and 0.5 g) was then added. The vials were pressurized with ethylene so that the final pressure would be 6.9 MPa at temperature (130° C.). After approximately 14 h, the reactions were cooled to RT and the gases vented. $^1$H NMR analyses of the samples gave the following yields of 1,3-propanediol diformate based on formaldehyde, as shown in Table 6.

TABLE 6

| Entry | Scandium Triflate (g) | 1,3-Propanediol diformate (%) |
|---|---|---|
| 1 | 0.1 | 46.9 |
| 2 | 0.2 | 60.33 |
| 3 | 0.3 | 57.46 |
| 4 | 0.4 | 39.13 |
| 5 | 0.5 | 37.57 |

EXAMPLE 56

Reaction of Ethylene, Paraformaldehyde, Formic acid and Scandium Triflate

In a dry box, formic acid (96%) (3.08 g) and paraformaldehyde (0.10 g) were added to each of 5 separate oven dried 25 mL vials. Scandium triflate (0.10, 0.2, 0.3, 0.4 and 0.5 g) was then added. The vials were pressurized with ethylene so that the final pressure would be 3.5 MPa at temperature (90° C.). After approximately 14 h, the reactions were cooled to RT and the gases vented. $^1$H NMR analyses of the samples gave the following yields of 1,3-propanediol diformate based on formaldehyde, as shown in Table 7.

TABLE 7

| Entry | Scandium Triflate (g) | 1,3-Propanediol diformate (%) |
|---|---|---|
| 1 | 0.1 | 33.52 |
| 2 | 0.2 | 33.52 |
| 3 | 0.3 | 34.01 |
| 4 | 0.4 | 25.55 |
| 5 | 0.5 | 35.41 |

EXAMPLE 57

Reaction of Ethylene, Formaldehyde (37%), Formic acid and Scandium Triflate

In a dry box, formic acid (96%) (3.08 g) and formaldehyde (37%, 0.270 g) were added to each of 5 separate oven dried 25 mL vials. Scandium triflate (0.10, 0.2, 0.3, 0.4, and 0.5 g) was then added. The vials were pressurized with ethylene so that the final pressure would be 6.9 MPa at temperature (130° C.). After approximately 14 h, the reactions were cooled to RT and the gases vented. $^1$H NMR analyses of the samples gave the following yields of 1,3-propanediol diformate based on formaldehyde, as shown in Table 8.

TABLE 8

| Entry | Scandium Triflate (g) | 1,3-Propanediol diformate (%) |
|---|---|---|
| 1 | 0.1 | 26.93 |
| 2 | 0.2 | 25.52 |
| 3 | 0.3 | 24.9 |
| 4 | 0.4 | 20.46 |
| 5 | 0.5 | 25.54 |

EXAMPLE 58

Reaction of Ethylene, Paraformaldehyde, Formic acid and Scandium Triflate

In a dry box, formic acid (96%) (3.08 g) and paraformaldehyde (0.10 g) were added to each of 5 separate oven dried 25 mL vials. Scandium triflate (0.01, 0.02, 0.03, 0.04 and 0.05 g) was then added. The vials were pressurized with ethylene so that the final pressure would be 6.9 MPa at temperature (130° C.). After approximately 14 hours, the reactions were cooled to RT and the gases vented. $^1$H NMR analyses of the samples gave the following yields of 1,3-propanediol diformate based on formaldehyde, as shown in Table 9.

TABLE 9

| Entry | Scandium Triflate (g) | 1,3-Propanediol diformate (%) |
|---|---|---|
| 1 | 0.01 | 26.5 |
| 2 | 0.02 | 58.91 |
| 3 | 0.03 | 67.49 |
| 4 | 0.04 | 36.31 |
| 5 | 0.05 | 37.97 |

EXAMPLE 59

Reaction of Ethylene, Paraformaldehyde, Formic acid and Ytterbium Triflate

In a dry box, formic acid (96%) (3.08 g) and paraformaldehyde (0.10 g) were added to each of 5 separate oven dried 25 mL vials. Ytterbrium triflate (0.10, 0.2, 0.3, 0.4 and 0.5 g) was then added. The vials were pressurized with ethylene so that the final pressure would be 6.9 MPa at temperature (130° C.). After approximately 14 h, the reactions were cooled to RT and the gases vented. $^1$H NMR analyses of the samples gave the following yields of 1,3-propanediol diformate based on formaldehyde, as shown in Table 10.

TABLE 10

| Entry | Ytterbium Triflate (g) | 1,3-Propanediol diformate (%) |
|---|---|---|
| 1 | 0.1 | 34.38 |
| 2 | 0.2 | 58.8 |
| 3 | 0.3 | 35.03 |

TABLE 10-continued

| Entry | Ytterbrium Triflate (g) | 1,3-Propanediol diformate (%) |
|---|---|---|
| 4 | 0.4 | 61.22 |
| 5 | 0.5 | 29.28 |

EXAMPLE 60

Reaction of Ethylene, Paraformaldehyde, Formic acid and Ytterbrium Triflate

In a dry box, formic acid (96%) (3.08 g) and paraformaldehyde (0.10 g) were added to each of 5 separate oven dried 25 mL vials. Ytterbrium triflate (0.10, 0.2, 0.3, 0.4 and 0.5 g) was then added. The vials were pressurized with ethylene so that the final pressure would be 6.9 MPa at temperature (90° C.). After approximately 14 h, the reactions were cooled to RT and the gases vented. $^1$H NMR analyses of the samples gave the following yields of 1,3-propanediol diformate based on formaldehyde, as shown in Table 11.

TABLE 11

| Entry | Ytterbrium Triflate (g) | 1,3-Propanediol diformate (%) |
|---|---|---|
| 1 | 0.1 | 30.1 |
| 2 | 0.2 | 39.81 |
| 3 | 0.3 | 34.03 |
| 4 | 0.4 | 28.34 |
| 5 | 0.5 | 34.5 |

EXAMPLE 61

Reaction of Ethylene, Formaldehyde (37%), Formic acid and Ytterbrium Triflate

In a dry box, formic acid (96%) (3.08 g) and formaldehyde (37%, 0.270 g) were added to each of 3 separate oven dried 25 mL vials. Ytterbrium triflate (0.10, 0.2, and 0.3 g) was then added. The vials were pressurized with ethylene so that the final pressure would be 6.9 MPa at temperature (130° C.). After approximately 14 h, the reactions were cooled to RT and the gases vented. $^1$H NMR analyses of the samples gave the following yields of 1,3-propanediol diformate based on formaldehyde, as shown in Table 12.

TABLE 12

| Entry | Ytterbrium Triflate (g) | 1,3-Propanediol diformate (%) |
|---|---|---|
| 1 | 0.1 | 23.69 |
| 2 | 0.2 | 25.21 |
| 3 | 0.3 | 22.69 |

EXAMPLE 62

Reaction of Ethylene, Formaldehyde (37%), Formic acid and Neodymium Triflate

In a dry box, formic acid (96%) (3.08 g) and formaldehyde (37%, 0.270 g) were added to each of 3 separate oven dried 25 mL vials. Neodymium triflate (0.10, 0.2, and 0.3 g) was then added. The vials were pressurized with ethylene so that the final pressure would be 6.9 MPa at temperature (130° C.). After approximately 14 h, the reactions were cooled to RT and the gases vented. $^1$H NMR analyses of the samples gave the following yields of 1,3-propanediol diformate based on formaldehyde, as shown in Table 13.

TABLE 13

| Entry | Neodymium Triflate (g) | 1,3-Propanediol diformate (%) |
| --- | --- | --- |
| 1 | 0.1 | 19.66 |
| 2 | 0.2 | 40.53 |
| 3 | 0.3 | 43.21 |

EXAMPLE 63

Reaction of Ethylene, Paraformaldehyde, Toluic Acid and Scandium Triflate

In a dry box, toluic acid (5.40 g) and paraformaldehyde (0.10 g) were added an oven dried 25 mL vial. Scandium triflate (0.30 g) was then added. The vial was pressurized with ethylene so that the final pressure would be 6.9 MPa at temperature (200° C.). After approximately 14 h, the reaction was cooled to RT and the gases vented. The resulting material was dissolved in methylene chloride (~50 mL), the resulting solution was washed with 5% NaOH (2×25 mL), and then water (25 mL) and then dried over anhydrous sodium sulfate. The sulfate was removed via filtration and the organic liquid concentrated at reduced pressure. The resulting concentrate was column chromatography (~2.5×31 cm), silica gel 60, hexanes/ethyl acetate (9/1), $R_f$: 0.36, affording 0.06 g of 1,3-propanediol diester of toluic acid. $^{13}$C NMR (CDCl$_3$): 166.55 (C=O), 143.57 and 127.33 (quat Ar C's), 129.56 and 129.00 (Ar CH's), 61.52 (O—CH$_2$), 28.26 (O—C—CH$_2$—C—O) and 21.57 (Ar—CH$_3$).

EXAMPLE 64

Reaction of Ethylene, Paraformaldehyde, Toluic Acid and Scandium Triflate

In a dry box, toluic acid (5.40 g) and paraformaldehyde (0.10 g) were added an oven dried 25 mL vial. Scandium triflate (0.10 g) was then added. The vial was pressurized with ethylene so that the final pressure would be 6.9 MPa at temperature (200° C.). After approximately 14 h, the reaction was cooled to RT and the gases vented. The resulting material was dissolved in methylene chloride (~50 mL), the resulting solution was washed with 5% NaOH (2×25 mL), and then water (25 mL) and then dried over anhydrous sodium sulfate. The sulfate was removed via filtration and the organic liquid concentrated at reduced pressure. The resulting concentrate was column chromatography (~2.5×30 cm), silica gel 60, hexanes/ethyl acetate (9/1), $R_f$: 0.36, affording 0.11 g of 1,3-propanediol diester of toluic acid.

EXAMPLE 65

Reaction of Ethylene, Paraformaldehyde, Formic acid and Ytterbium Triflate

In a dry box, formic acid (96%) (3.08 g) and paraformaldehyde (0.10 g) were added to each of 5 separate oven dried 25 mL vials. Ytterbrium triflate (0.01, 0.02, 0.03, 0.04 and 0.05 g) was then added. The vials were pressurized with ethylene so that the final pressure would be 3.5 MPa at temperature (150° C.). After approximately 14 h, the reactions were cooled to RT and the gases vented. $^1$H NMR analyses of the samples gave the following yields of 1,3-propanediol diformate based on formaldehyde.

TABLE 14

| Entry | Ytterbrium Triflate (g) | 1,3-Propanediol diformate (%) |
| --- | --- | --- |
| 1 | 0.01 | 34.81 |
| 2 | 0.02 | 33.69 |
| 3 | 0.03 | 35.36 |
| 4 | 0.04 | 32.83 |
| 5 | 0.05 | 23.3 |

EXAMPLE 66

Reaction of Ethylene, Paraformaldehyde, Formic acid and Scandium Triflate

In a dry box, formic acid (96%) (3.08 g) and paraformaldehyde (0.10 g) were added to each of 5 separate oven dried 25 mL vials. Scandium triflate (0.01, 0.02, 0.03, 0.04 and 0.05 g) was then added. The vials were pressurized with ethylene so that the final pressure would be 6.9 MPa at temperature (150° C.). After approximately 14 h, the reactions were cooled to RT and the gases vented. $^1$H NMR analyses of the samples gave the following yields of 1,3-propanediol diformate based on formaldehyde, as shown in Table 15.

TABLE 15

| Entry | Scandium Triflate (g) | 1,3-Propanediol diformate (%) |
| --- | --- | --- |
| 1 | 0.01 | 33.7 |
| 2 | 0.02 | 35.73 |
| 3 | 0.03 | 36.08 |
| 4 | 0.04 | 36.1 |
| 5 | 0.05 | 34.97 |

EXAMPLE 67

Reaction of Ethylene, 37% Formaldehyde, Formic acid and Nafion® NR50

In a dry box, formic acid (96%) (3.08 g) and paraformaldehyde (0.27 g) were added to each of five separate oven dried 25 mL vials. Nafion® NR50 (a perfluorinated polymer containing perfluoroalkylsulfonic acid side chains available from E. I. du Pont de Nemours and Company, Wilmington, Del., 19880, U.S.A.) (0.01, 0.02, 0.03, 0.04 and 0.05 g) was then added. The vials were pressurized with ethylene so that the final pressure would be 6.9 MPa at temperature (130° C.). After approximately 14 h, the reactions were cooled to RT and the gases vented. $^1$H NMR analyses of the samples gave the following yields of 1,3-propanediol diformate based on formaldehyde, as shown in Table 16.

TABLE 16

| Entry | Nafion ® NR50 (g) | 1,3-Propanediol diformate (%) |
| --- | --- | --- |
| 1 | 0.01 | 27 |
| 2 | 0.02 | 21.88 |
| 3 | 0.03 | 23.99 |
| 4 | 0.04 | 25.65 |
| 5 | 0.05 | 22.72 |

EXAMPLE 68

Reaction of Ethylene, Paraformaldehyde, Formic acid and Hafnium Triflate

In a dry box, formic acid (96%) (3.08 g) and paraformaldehyde (0.10 g) were added to each of 5 separate oven dried 25 mL vials. Hafnium triflate (0.10, 0.2, 0.3, 0.4 and 0.5 g) was then added. The vials were pressurized with ethylene so that the final pressure would be 6.9 MPa at temperature (90° C.). After approximately 14 h, the reactions were cooled to RT and the gases vented. $^1$H NMR analyses of the samples gave the following yields of 1,3-propanediol diformate based on formaldehyde, as shown in Table 17.

TABLE 17

| Entry | Hafnium Triflate (g) | 1,3-Propanediol diformate (%) |
|---|---|---|
| 1 | 0.1 | 21.28 |
| 2 | 0.2 | 31.34 |
| 3 | 0.3 | 37.7 |
| 4 | 0.4 | 26.61 |
| 5 | 0.5 | 30.31 |

EXAMPLE 69

Reaction of Ethylene, Paraformaldehyde, Formic acid and Bismuth Triflate

In a dry box, formic acid (96%) (3.08 g) and paraformaldehyde (0.10 g) were added to each of 5 separate oven dried 25 mL vials. Bismuth triflate (0.01, 0.02, 0.03, 0.04 and 0.05 g) was then added. The vials were pressurized with ethylene so that the final pressure would be 6.9 MPa at temperature (90° C.). After approximately 14 h, the reactions were cooled to RT and the gases vented. $^1$H NMR analyses of the samples gave the following yields of 1,3-propanediol diformate based on formaldehyde, as shown in Table 18.

TABLE 18

| Entry | Bismuth Triflate (g) | 1,3-Propanediol diformate (%) |
|---|---|---|
| 1 | 0.01 | 29.41 |
| 2 | 0.02 | 22.71 |
| 3 | 0.03 | 32.9 |
| 4 | 0.04 | 27.13 |
| 5 | 0.05 | 48.49 |

EXAMPLE 70

Reaction of Ethylene, 37% Formaldehyde, Formic acid and Lanthanum Tris(trifluoroacetate)

In a dry box, formic acid (96%) (3.08 g) and 37% formaldehyde (0.270 g) were added to each of 5 separate oven dried 25 mL vials. Lanthanum tris(trifluoroacetate) (0.01, 0.02, 0.03, 0.04 and 0.05 g) was then added. The vials were pressurized with ethylene so that the final pressure would be 6.9 MPa at temperature (90° C.). After approximately 14 h, the reactions were cooled to RT and the gases vented. $^1$H NMR analyses of the samples gave the following yields of 1,3-propanediol diformate based on formaldehyde, as shown in Table 19.

TABLE 19

| Entry | Lanthanum Tris(trifluoroacetate) (g) | % 1,3-Propanediol diformate |
|---|---|---|
| 1 | 0.01 | 13.74 |
| 2 | 0.02 | 19.85 |
| 3 | 0.03 | 20.31 |

TABLE 19-continued

| Entry | Lanthanum Tris(trifluoroacetate) (g) | % 1,3-Propanediol diformate |
|---|---|---|
| 4 | 0.04 | 21.03 |
| 5 | 0.05 | 20.5 |

EXAMPLE 71

Reaction of Ethylene, Paraformaldehyde, Formic acid and Yttrium Tris(benzenesulfonate)

In a dry box, formic acid (96%) (3.08 g) and paraformaldehyde (0.10 g) added to each of 5 separate oven dried 25 mL vials. Yttrium benzenesulfonate) (0.01, 0.02, 0.03, 0.04 and 0.05 g) was then added. The were pressurized with ethylene so that the final pressure would be 6.9 MPa at temperature (90° C.). After approximately 14 h, the reactions were cooled to RT and the gases vented. $^1$H NMR analyses of the samples gave the following yields of 1,3-propanediol diformate based on formaldehyde, as shown in Table 20.

TABLE 20

| Entry | Yttrium Tris(benzenesulfonate) (g) | % 1,3-Propanediol diformate |
|---|---|---|
| 1 | 0.01 | 46.37 |
| 2 | 0.02 | 30.05 |
| 3 | 0.03 | 36.63 |
| 4 | 0.04 | 32.25 |
| 5 | 0.05 | 33.38 |

What is claimed is:

1. A process for manufacturing an ester of 1,3-propanediol, comprising, contacting at a temperature of about 0° C. to about 250° C., ethylene, formaldehyde or a form of formaldehyde, a carboxylic acid, and a compound of the formula $MZ_n \cdot Q_t$, wherein:

M is a zirconium[IV], cobalt[II], vanadium[IV], bismuth [II], tin[II], a rare earth metal, scandium or yttrium;

n is the oxidation state of M;

at least one of Z is an anion of the formula $R^1SO_3^-$ or $R^1CO_2^-$, wherein $R^1$ is hydrocarbyl or substituted hydrocarbyl containing 1 to 20 carbon atoms or part of a polymer, and the remainder of Z is oxo or one or more monovalent anions;

Q is a neutral ligand; and t is 0 or an integer of 1 to 12.

2. The process as recited in claim 1 wherein at least one of Z is $R^1SO_3^-$.

3. The process as recited in claim 1 wherein all of Z are $R^1SO_3^-$.

4. The process as recited in claims 1, 2 or 3 wherein $R^1$ is trifluoromethyl.

5. The process as recited in claim 1 wherein $R^1$ is perfluoroalkyl containing 1 to 12 carbon atoms, and optionally containing one or more ether groups, or part of a fluorinated polymer wherein the carbon atoms alpha and beta to the sulfonate or carboxylate group are together bonded to at least 4 fluorine atoms, or when $R^1SO_3^-$ is present $R^1$ is aryl or substituted aryl.

6. The process as recited in claim 3 wherein $R^1$ is perfluoroalkyl containing 1 to 12 carbon atoms, and optionally containing one or more ether groups, part of a fluorinated polymer wherein the carbon atoms alpha and beta to the sulfonate or carboxylate group are together bonded to at least 4 fluorine atoms, or is aryl or substituted aryl.

7. The process as recited in claim 1 wherein M is a rare earth metal, scandium or yttrium.

8. The process as recited in claim 6 wherein M is a rare earth metal, scandium or yttrium.

9. The process as recited in claims 1, 2, 3 or 7 wherein said carboxylic acid is monofunctional.

10. The process as recited in claim 9 wherein said carboxylic acid is acetic acid or formic acid.

11. The process as recited in claim 9 wherein said carboxylic acid is formic acid.

12. The process as recited in claim 1 wherein said carboxylic acid is formic acid.

13. The process as recited in claim 1 wherein t is 0.

14. The process as recited in claims 1 or 12 wherein said temperature is about 50° C. to about 175° C.

15. The process as recited in claim 11 wherein said temperature is about 50° C. to about 175° C.

16. The process as recited in claim 1 wherein an ethylene pressure is about 700 kPag to about 10 MPag.

17. The process as recited in claims 1 or 3 wherein a molar ratio said carboxylic acid:said formaldehyde is about 2:1 to about 15:1.

18. The process as recited in claim 1 wherein said carboxylic acid is difunctional and an oligomer or polymer of said carboxylic acid and 1,3-propanediol is produced.

19. An improved process for the production of an ester by the Prins reaction by reacting an olefin, formaldehyde or a form of formaldehyde, and a carboxylic acid and optionally in the presence of a Lewis or Bronsted acid catalyst, wherein the improvement comprises, using formic acid as the carboxylic acid.

20. The process as recited in claim 19 wherein a Lewis acid catalyst is used.

21. The process as recited in claim 19 wherein a Bronsted acid catalyst is used.

22. The process as recited in claim 19 wherein a Lewis or Bronsted acid is not present.

23. The process as recited in claims 19, 20, 21 or 22 wherein said olefin is ethylene.

* * * * *